US012300389B2

(12) United States Patent
Kozloski et al.

(10) Patent No.: US 12,300,389 B2
(45) Date of Patent: May 13, 2025

(54) DIGITAL TWIN MANAGER (71) Applicant: INTERNATIONAL BUSINESS MACHINES CORPORATION, Armonk, NY (US)

(72) Inventors: James R. Kozloski, New Fairfield, CT (US); Michael S. Gordon, Yorktown Heights, NY (US); Sarbajit K. Rakshit, Kolkata (IN); Komminist Weldemariam, Ottawa (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 520 days.

(21) Appl. No.: 16/926,863

(22) Filed: Jul. 13, 2020

(65) Prior Publication Data
US 2022/0013199 A1  Jan. 13, 2022

(51) Int. Cl.
G16H 50/50 (2018.01)
A61B 5/055 (2006.01)
A61B 6/03 (2006.01)
G06F 18/21 (2023.01)
G16H 10/60 (2018.01)
G16H 50/20 (2018.01)

(52) U.S. Cl.
CPC .............. G16H 50/50 (2018.01); A61B 5/055 (2013.01); A61B 6/032 (2013.01); A61B 6/037 (2013.01); G06F 18/21 (2023.01); G16H 10/60 (2018.01); G16H 50/20 (2018.01)

(58) Field of Classification Search
CPC ........ G16H 10/60; G16H 50/20; G16H 50/50; A61B 5/055; A61B 6/032; A61B 6/037; G06K 9/6217
See application file for complete search history.

(56) References Cited

U.S. PATENT DOCUMENTS

| 9,881,430 | B1 | 1/2018 | Shah | |
| 2012/0197619 | A1* | 8/2012 | Namer Yelin | G16H 50/50 382/128 |
| 2015/0250934 | A1* | 9/2015 | Min | A61M 60/427 700/119 |
| 2017/0217102 | A1 | 8/2017 | Mansi | |

(Continued)

OTHER PUBLICATIONS

Albright, "The Promise of 3D Printing Organs", http://www.digitalengineering247.com/article/the-promise-of-3d-printing . . . , printed Dec. 31, 2019, pp. 1-7.

(Continued)

Primary Examiner — Robert A Sorey
Assistant Examiner — Kristine K Rapillo
(74) Attorney, Agent, or Firm — Amin, Turocy & Watson, LLP (57) ABSTRACT A method, a structure, and a computer system for digital twin management. The exemplary embodiments may include gathering data corresponding to one or more bodily tissues and generating one or more digital twin versions of the one or more bodily tissues. In addition, the exemplary embodiments may further include identifying a most appropriate digital twin version of the one or more digital twin versions based on a health and a compatibility of the one or more digital twin versions, and distributing the most appropriate digital twin version.

18 Claims, 5 Drawing Sheets

(56) References Cited

U.S. PATENT DOCUMENTS

| | | | | |
|---|---|---|---|---|
| 2019/0005195 | A1* | 1/2019 | Peterson | G16H 10/60 |
| 2019/0087544 | A1 | 3/2019 | Peterson | |
| 2019/0138970 | A1 | 5/2019 | Deutsch | |
| 2019/0156477 | A1 | 5/2019 | Perrin | |
| 2020/0203020 | A1* | 6/2020 | Cox | G16H 50/50 |
| 2021/0151187 | A1* | 5/2021 | Mansi | G16H 50/20 |
| 2021/0383892 | A1* | 12/2021 | Holzer | G16H 50/70 |

OTHER PUBLICATIONS

Goh, "How Digital Twins of the Human Body Can Advance Healthcare", Jul. 9, 2018, Hewlett Packard Enterprise, pp. 1-8.

Griffin, "Fanatical Futurist—Soldiers Digital Twins let US Army 3D Print Replacement Body Parts in Battle", Jan. 5, 2017, https://www.fanaticalfuturist.com/2017/01/digital-clones-will-let-us-army-3d-print-new-body-parts-in-battle-to-treat-injured-soldiers/, pp. 1-16.

Houten, "How a Virtual Heart Could Save Your Real One", LINKEDIN, https://www.linkedin.com/pulse/how-virtual-heart-could-save-your-real -. . . , Nov. 12, 2018, pp. 1-7.

Kennedy, "What is Digital Twins (+Impact on Business Modernization", http://learn.g2.com/trends/digital-twins, Jan. 18, 2018, pp. 1-3.

Malyala et al., "Organ Printing with Life Cells: A Review", Science Direct, https://www.sciencedirect.com/science/article/pii/S2214785317301220, vol. 4, Issue 2, Part A, 2017, pp. 1074-1083.

Mell et al., "The NIST Definition of Cloud Computing", National Institute of Standards and Technology, Special Publication 800-145, Sep. 2011, pp. 1-7.

Miskinis, "Improving Healthcare Using Medical Digital Twin Technology", https://www.challenge.org/insights/digital-twin-in-healthcare/, printed Dec. 31, 2019, pp. 1-8.

Shaer, "Soon, your Doctor Could Print a Human Organ on Demand", Smithsonian Magazine, May 2015, pp. 1-6.

Sirota, "3D Organ Printing, The Science Journal of the Lander College of Arts and Sciences", vol. 10, Touro College, Fall 2016, pp. 1-8.

Tubbesing, "Digital Twins Optimize 3D Metal Printing", Siemens, Dec. 5, 2018, pp. 1-2.

Youtube, How can Digital Twin technology improve your business ?—Digital Twin explained, http://www.youtube.com/watch?v=fE15oz33la8, printed Dec. 31, 2019, pp. 1-2.

https://www.hannovermesse.de/en/news/news-articles/digital-twins-opti . . . "Digital Twins Optimize 3D Metal Printing", printed Jul. 19, 2020, pp. 1-3.

https://www.hpcwire.com/solution_content/hpe/health-life-sciences/how . . . ,"HPC Wire", Jul. 17, 2020, pp. 1-15.

Kilic et al., Microphysiological Systems, "Organs-on-chip monitory: sensors and other strategies", (http://mps.amegroups.com/index) / vol. 2 (Sep. 2018) (http://mps.amegroups.com/issue/view/320) / Organs-on-chip monitoring: sensors and other strategies, pp. 1-49.

* cited by examiner

DIGITAL TWIN MANAGER

BACKGROUND

The exemplary embodiments relate generally to digital twins, and more particularly to digital twin management.

A digital twin is an exact digital replica of a product, process, or service. This living model creates a thread between the physical and digital world, and enables simulations, testing, modelling, monitoring, etc. Moreover, the integration of devices such as Internet of Things enabled devices allow for such digital twin generation based on data collected by IoT sensors. Like everything in the realm of IoT, data is the primary driver and the most invaluable output of digital twins. The sharing and analysis of digital twin data empowers companies to make decisions which directly impact their key performance indicators.

SUMMARY

The exemplary embodiments disclose a method, a structure, and a computer system for digital twin management. The exemplary embodiments may include gathering data corresponding to one or more bodily tissues and generating one or more digital twin versions of the one or more bodily tissues. In addition, the exemplary embodiments may further include identifying a most appropriate digital twin version of the one or more digital twin versions based on a health and a compatibility of the one or more digital twin versions and distributing the most appropriate digital twin version.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

A digital twin is an exact digital replica of a product, process, or service. This living model creates a thread between the physical and digital world, and enables simulations, testing, modelling, monitoring, etc. Moreover, the integration of devices such as Internet of Things enabled devices allow for such digital twin generation based on data collected by IoT sensors. Like everything in the realm of IoT, data is the primary driver and most invaluable output of digital twins. The sharing and analysis of digital twin data empowers companies to make decisions which directly impact their key performance indicators.

Human body organs can be artificially made with 4D printing, and the same can be used for transplantation or for constructing resin models to aid in surgery or diagnosis. In the former case, when an organ needs to be replaced with an artificially built organ, various parameters are to be considered so that the artificial organ is compatible with the patient. In the case of surgical models, the organ may be rendered in a way that best represent its likely or most informative state at the time of surgery. Additionally, surgical models of bones, muscles, joints, tendons, etc. of an individual can be fabricated. A digital twin generating system can play a major role as it is capable of providing an exact working replica of a human body part such that exactly the same body parts or similar can be made with 3D or 4D printing. Moreover, an IoT enabled system and sensors can be used for seamlessly synchronizing the digital twin with its physical twin or model.

The present invention discloses the creation and versioning of digital twins for human organs based on computed health indexes and compatible metrics (e.g., organ size, shape, etc.) with respect to other organs. When an organ needs to be printed, either as a 3D tissue, a 3D model, etc., the best-known digital twin of an organ with respect to health and compatibility to other organs will be identified and printed for organ transplantation or surgery. In one embodiment, the digital twin is created using streams of data from IoT devices or sensors connected to personal data sources. The system stores and versions the healthiest digital twin of different organs such that when organ transplantation is required, the organ can be printed as per the best known healthiest digital twin of the organ. In order to identify a healthiest and most compatible organ with respect to a patient for printing, a health score and compatibility score for each organ is computed every time a state or change is detected in the physical world. The digital twin versions of an organ may then be referenced and/or printed as needed. A detailed description of the invention follows.

Figure 1:
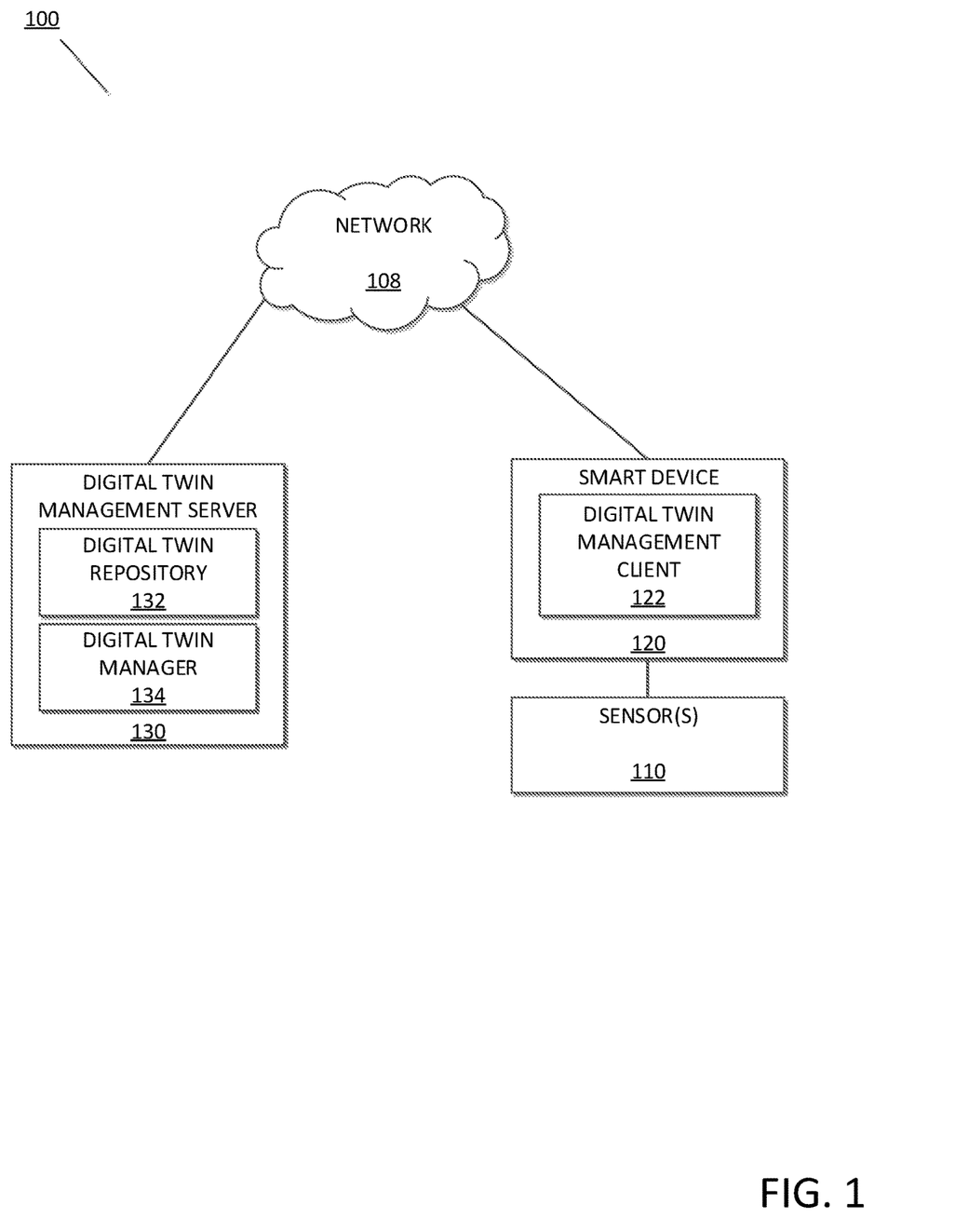
FIG. 1 depicts an exemplary schematic diagram of a digital twin management system 100, in accordance with the exemplary embodiments.

FIG. 1 depicts the digital twin management system 100, in accordance with exemplary embodiments. According to the exemplary embodiments, the digital twin management system 100 may include sensor(s) 110, a smart device 120, and a digital twin management server 130, which all may be interconnected via a network 108. While programming and data of the exemplary embodiments may be stored and accessed remotely across several servers via the network 108, programming and data of the exemplary embodiments may alternatively or additionally be stored locally on as few as one physical computing device or amongst other computing devices than those depicted. For example, in some embodiments, the sensor(s) 110 may be incorporated into the smart device 120 and communicate directly with the network 108. In other embodiments, the components of the digital twin management server 130 may be incorporated into the smart device 120 for local operation. The operations of the digital twin management system 100 are described in greater detail herein.

In the exemplary embodiments, the network 108 may be a communication channel capable of transferring data between connected devices. In the exemplary embodiments, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a Bluetooth network, a Wi-Fi network, or a combination thereof. The network 108 may operate in frequencies including 2.4 GHz and 5 GHz internet, near-field communication, Z-Wave, Zigbee, etc. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices.

In exemplary embodiments, the sensor(s) 110 may be one or more devices capable of collecting data. In particular, the sensor(s) 110 may be configured to collect data with respect to one or more user body parts, including organs, bones, tissue, muscles, joints, tendons, tumours, etc. For example, the organs for which data is collected may include the kidney, liver, spleen, lung, thymus, pancreas, gall bladder, neuronal structures, heart, ear, and eye. In addition, the digital twin manager 134 may further break down organs into their component parts, for example the inner ear, facial components, mouth components including teeth, etc. The data collected for the body parts may include a size, shape, position, orientation, range of motion (including displacement), flexibility, contraction, torsion, inflation, response of tissue to ultrasound, composition, etc. of such body parts.

Accordingly, in order to collect said data, the sensor(s) 110 may be medical imaging devices, for example machines capable of performing a magnetic resonance imaging (MRI) scan, a positron emission tomography (PET) scan, an x-ray, CT/CAT scan, an ultrasound device, an echocardiography device, an electroencephalograph (EEG/EcoG), a magnetoencephalography (MEG), an electrocardiograph (ECG), etc. In addition, the sensor(s) 110 may be smart devices such as a smart appliance or bed, as well as portable or wearable devices such as a smart watch/wristband, glasses, auscultatory device, contact lens, ring, mouthpiece, adhesives, phone or computer (e.g., embodied by the smart device 120), etc. Moreover, the sensor(s) 110 may be special purpose or medical devices such as an insulin pen, pacemaker, catheter, implantable device, ingestible device (e.g., CAP-scan), etc. In embodiments, the sensor(s) 110 may communicate with the smart device 120 and/or network 108 through means such as WiFi, Bluetooth, Near Field communicating (NFC), etc. In general, the sensor(s) 110 may be any device capable of collecting data relating to the generation of one or more digital twin versions. The sensor(s) 110 are described in greater detail with respect to FIG. 2-5.

In exemplary embodiments, the smart device 120 includes a digital twin management client 122, and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of sending and receiving data to and from other computing devices. While the smart device 120 is shown as a single device, in other embodiments, the smart device 120 may be comprised of a cluster or plurality of computing devices, in a modular manner, etc., working together or working independently. The smart device 120 is described in greater detail as a hardware implementation with reference to FIG. 3, as part of a cloud implementation with reference to FIG. 4, and/or as utilizing functional abstraction layers for processing with reference to FIG. 5.

The digital twin management client 122 may act as a client in a client-server relationship, and may be a software and/or hardware application capable of communicating with and providing a user interface for a user to interact with a server and other computing devices via the network 108. Moreover, in the example embodiment, the digital twin management client 122 may be capable of transferring data from the smart device 120 to and from other devices via the network 108. In embodiments, the digital twin management client 122 may utilize various wired and wireless connection protocols for data transmission and exchange, including Bluetooth, 2.4 GHz and 5 GHz internet, near-field communication, Z-Wave, Zigbee, etc. The digital twin management client 122 is described in greater detail with respect to FIG. 2-5.

In exemplary embodiments, the digital twin management server 130 includes a digital twin repository 132 and a digital twin manager 134 and may act as a server in a client-server relationship with the digital twin management client 122. The digital twin management server 130 may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of sending and receiving data to and from other computing devices. While the digital twin management server 130 is shown as a single device, in other embodiments, the digital twin management server 130 may be comprised of a cluster or plurality of computing devices, in a modular manner, etc., working together or working independently. The digital twin management server 130 is described in greater detail as a hardware implementation with reference to FIG. 3, as part of a cloud implementation with reference to FIG. 4, and/or as utilizing functional abstraction layers for processing with reference to FIG. 5.

The digital twin repository 132 may be one or more databases detailing one or more versions of one or more digital twins of body parts corresponding to one or more users. In embodiments, the digital twin repository 132 may store information detailing the digital twins corresponding to one or more user organs, bones, tissue, muscles, joints, tendons, tumours, etc. For example, the organs for which data is stored may include the kidney, liver, spleen, lung, thymus, pancreas, gall bladder, neuronal structures, heart, ear, and eye. In addition, the digital twin manager 134 may further break down organs into their component parts, for example the inner ear, facial components, mouth components including teeth, etc. The data stored for the body parts may include a size, shape, position, orientation, range of motion (including displacement), flexibility, contraction, torsion, inflation, response of tissue to ultrasound, composition, etc. of such body parts. The digital twin repository 132 may store the digital twins with respect to each patient for one or more body parts, and each body part may have multiple digital twin versions corresponding to different times throughout the life of the user. As such, the digital twin management system 100 may be capable of selecting an appropriate version of a digital twin when needed based on a healthiness of the version, compatibilities with current user body parts (e.g., size), etc., as is described in greater detail forthcoming.

The digital twin manager 134 may be a software and/or hardware program that may be capable of collecting user body part data and generating one or more digital twin versions of the body parts. The digital twin manager 134 may be further capable of analysing the body part data as well as determining whether a digital twin is needed. Based on determining that the digital twin is needed, the digital twin manager 134 may select an appropriate digital twin version and distribute the appropriate digital twin version. The digital twin manager 134 is described in greater detail with reference to FIG. 2-5.

Figure 2:
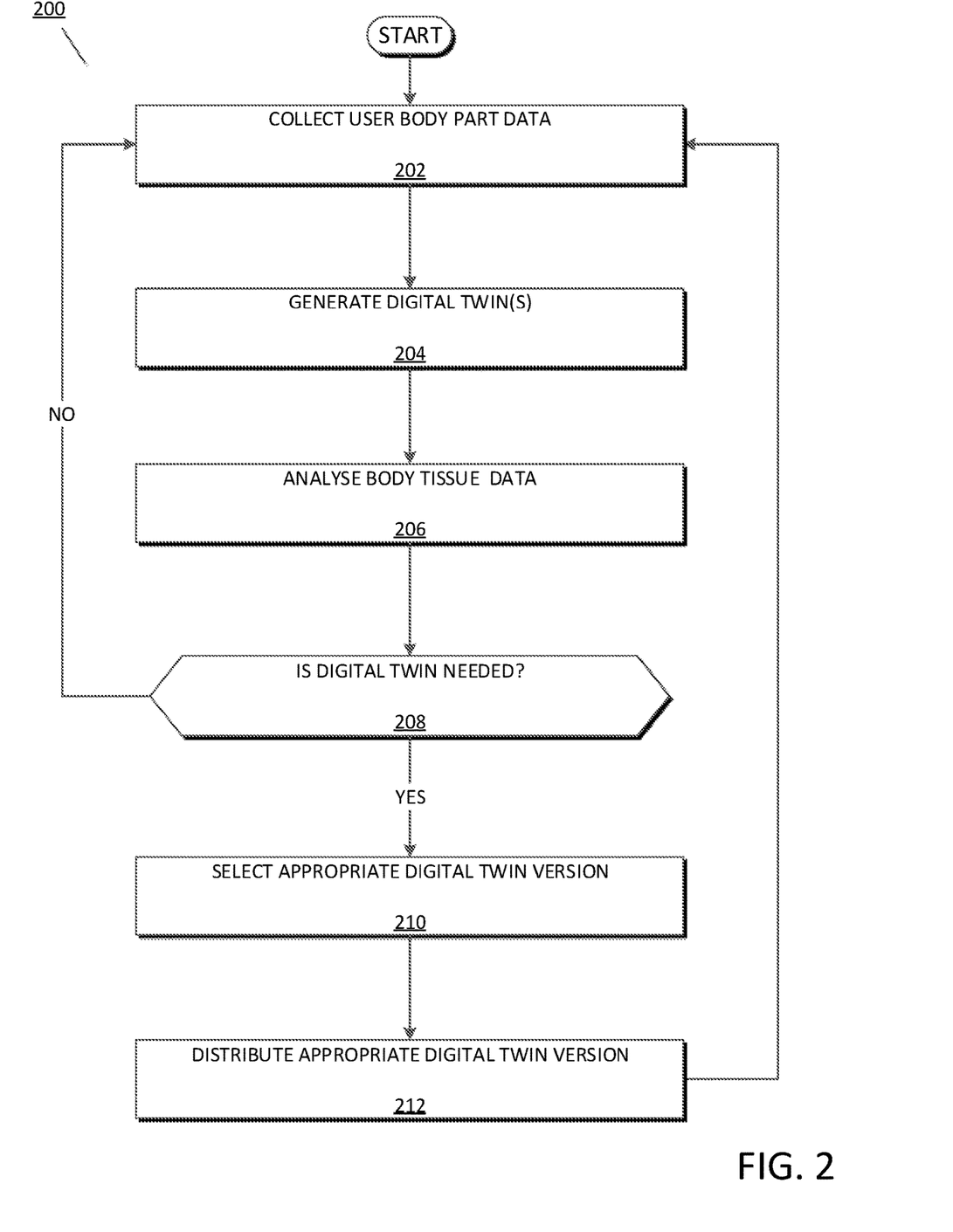
FIG. 2 depicts an exemplary flowchart 200 illustrating the operations of a digital twin manager 134 of the digital twin management system 100, in accordance with the exemplary embodiments.

FIG. 2 depicts an exemplary flowchart 200 illustrating the operations of the digital twin manager 134 of the digital twin management system 100, in accordance with the exemplary embodiments.

The digital twin manager 134 may collect user tissue data (step 202). In exemplary embodiments, the digital twin manager 134 may first collect user body part data in order to generate a first version of one or more digital twins corresponding to user organs, bones, tissue, muscles, joints, tendons, tumours, etc. The digital twin manager 134 may collect such data using the smart device 120 and/or the one or more sensors 110, for example via an x-ray, CT scan, MRI, ingestible device, smart watch, etc. In addition, the digital twin manager 134 may collect user body part information via reference to a health record, for example a scanned hard copy or an electronic health/medical record. In embodiments, the digital twin manager 134 may initialize collecting user body part data at any time within the life of a user, for example at birth or adolescence, and may thereafter continuously collect user body part data indefinitely or until a specific age or occurrence. Depending on a type of body part for which data is collected, the user body part data may include a size, shape, position, orientation, range of motion (including displacement), flexibility, contraction, torsion, inflation, response of tissue to ultrasound, radiation, composition, compatibilities, and other features relative to the body part/body of the user. An illustrative example includes the size and position of a user's lungs which change during inspiration and expiration.

In order to better illustrate the operations of the digital twin manager 134, reference is now made to an illustrative example wherein the digital twin manager 134 processes an echocardiographic report to extract data relating to the heart of a user, including but not limited to a size of the left and right ventricles as well as a mean and peak velocity of the aortic, mitral, tricuspid, and pulmonic valves.

The digital twin manager 134 may generate digital twin versions corresponding to the user body parts (step 204). Based on the collected user body part data, the digital twin manager 134 may generate digital twin versions of the body parts and store them in association with the body parts of the user within the digital twin repository 132, thereby creating successive and synchronized digital twin versions of the user body parts. In embodiments, the digital twin repository 132 may store any number of digital twin versions corresponding to a body part of a user, and the generated digital twins may include information with respect to the body part such as a timestamp corresponding to when the body part was analysed as well as characteristics of the body part itself collected above, including a size, shape, position, orientation, composition, compatibilities, etc.

In furthering the illustrative example introduced above, the digital twin manager 134 generates a digital twin version detailing a date at which the organ was generated/synchronized and the collected data, including the size of the left and right ventricles as well as the mean and peak velocity of the aortic, mitral, tricuspid, and pulmonic valves. If the user has previous and existing digital twin versions of the heart, the currently generated version is added as a subsequent version to those existing versions.

The digital twin manager 134 may analyse the body tissue data (step 206). In embodiments, the digital twin manager 134 may analyse the collected body part data (and corresponding digital twin data) in order to monitor changes and an overall evolution of the body parts as the user changes over time. Such analysis includes identifying changes in characteristics such as size, shape, composition, contractile efficiency, range of motion, tissue integrity, inflation range, dimensions and shape of surrounding body cavity, proximity to surrounding tissue, etc., as well as compatibilities with other body parts of the user. In an example, the size and position of a tumor could be determined by medical imaging (CTscan, PET, X-ray) and a digital twin could be formed to aid in their surgical removal or to position a Proton therapy beam relative to the patient for irradiation treatment. The digital twin, and the data on the current size, position, and reduction of size with radiation therapy, could be stored. The digital twin manager 134 may then store the body part evolution with respect to each digital twin version such that the changes may be considered and validated for compatibility when determining an appropriate version of the digital twin to distribute when needed (described in greater detail forthcoming).

Returning to the earlier-introduced example, the digital twin manager 134 analyses the body tissue data by comparing the generated digital twin version with precedent versions of the digital twin. Here, the digital twin manager 134 identifies differences in size of the left and right ventricles, as well as changes in the mean and peak velocity of the aortic, mitral, tricuspid, and pulmonic valves.

The digital twin manager 134 may determine whether a digital twin is needed (decision 208). In embodiments, the digital twin manager 134 may determine that a digital twin is needed in response to a request by a user or administrator. In other embodiments, the digital twin manager 134 may be configured to automatically detect when a digital twin is needed. For example, the digital twin manager 134 may be configured to detect when the failure of a body part such as the heart has occurred or is imminent via reference to a pacemaker, heart beat monitor, blood pressure monitor, or other device comprising the sensors 110. Earlier conditions for detection may include a threshold crossed wherein failure, though not imminent, is inevitable. This may include months or even years lead time. Conditions for detection events may include a function that aims to optimize the combination of 1) certainty about eventual failure, 2) risk of replacement, 3) degree of tissue compensation expected before failure, and 4) risk associated with compensation. In this way, the replacement may be ordered in order to prevent unwanted compensation by other bodily tissues as the targeted tissue begins down the path to failure.

With reference again to the formerly introduced example, the digital twin manager 134 may receive a user input from a medical professional indicating that the patient requires the replacement of a heart or portion thereof. Alternatively, the digital twin manager 134 may determine that the patient requires a replacement heart, or portion thereof, based on a function incorporating a certainty of eventual heart failure, risk of heart replacement, degree of tissue compensation expected before heart failure, and risk associated with such tissue compensation.

The digital twin manager 134 may select an appropriate digital twin version (step 210). Because the digital twin management system 100 is configured to collect data for and store multiple versions of a body tissue, the digital twin manager 134 may be configured to select a most appropriate version of the digital twin when it is determined that a digital twin is needed. In embodiments, the digital twin manager 134 may select an appropriate digital twin version based on one or more health features of the digital twin versions and/or one or more compatibility features between the digital twin versions and body parts of an intended user. The combination of these two features in selecting a digital twin may require optimization of a function, and take into account compensation underwent previously by other bodily tissues. Though often dependent on the type of body part, a health feature of the digital twin may include overall health, productivity, efficiency, blockages (e.g., arteries, etc.), range of motion, tissue viability, inflation properties, contractility, constituent cellular profiles (e.g., selective degeneration in a neural circuit), blood perfusion, interstitial concentrations of ions and macromolecules, lack/presence of tumours/abnormalities, identification of bottlenecks in pipelines, etc. In addition, the compatibility features may represent how compatible features of the digital twin versions (e.g., size, shape, position, orientation, composition, etc.) are with the current or future organs of the intended user. Compatibility may be a measure of physical shape and points of contact, or can include systemic factors, such as lung capacity vs. heart contractility, flow rates, etc. In embodiments, the digital twin manager 134 may note an absence or presence of a feature binarily while, in others, the digital twin manager 134 may correspondingly score the health features and compatibility features.

Having identified and/or scored the health features and compatibility features of the digital twin versions (step 210 continued), the digital twin manager 134 may select a most appropriate digital twin version based thereon. In embodiments, the digital twin manager 134 may determine a most appropriate digital twin version based on receiving suitable parameters of the one or more features (e.g., a range or threshold) from a user or administrator, then identifying the digital twin versions which fall into those parameters. In other embodiments, the digital twin manager 134 may select a most appropriate digital twin based on a score and/or presence of the one or more features (similarly selected by the user/administrator), for example a best overall health score, a best size compatibility score, and/or the absence of a tumour. Alternatively, the digital twin manager 134 may determine a most appropriate digital twin version using a model, for example one trained through techniques such as machine learning, including regression methods, Random Forest, Markov Chain Monte Carlo, and neural networks. In such embodiments, the digital twin manager 134 may weight the aforementioned features based on training data in a model that identifies and consolidates the features of a digital twin version into a score indicative of appropriateness. The digital twin manager 134 may then select the digital twin version having the best appropriateness score.

In furthering the example introduced above, the digital twin manager 134 implements a model that considers health features and compatibility features in order to determine an overall appropriateness score for multiple versions of the user heart, then selects a version of the heart having a highest appropriateness score.

The digital twin manager 134 may distribute the appropriate digital twin (step 212). In embodiments, the distribution of the appropriate digital twin may include transmitting the digital twin from the digital twin repository 132 to other computing devices and/or printing devices, organ banks, or synthetic part fabrication unit (e.g., an artificial knee fabrication unit), etc. For example, the digital twin manager 134 may transmit the appropriate digital twin to a one-, two-, three-, or four-dimensional printer for printing.

Concluding the aforementioned example, the digital twin manager 134 transmits the version of the user heart having a highest appropriateness score to an artificial heart fabrication unit.

Figure 3:
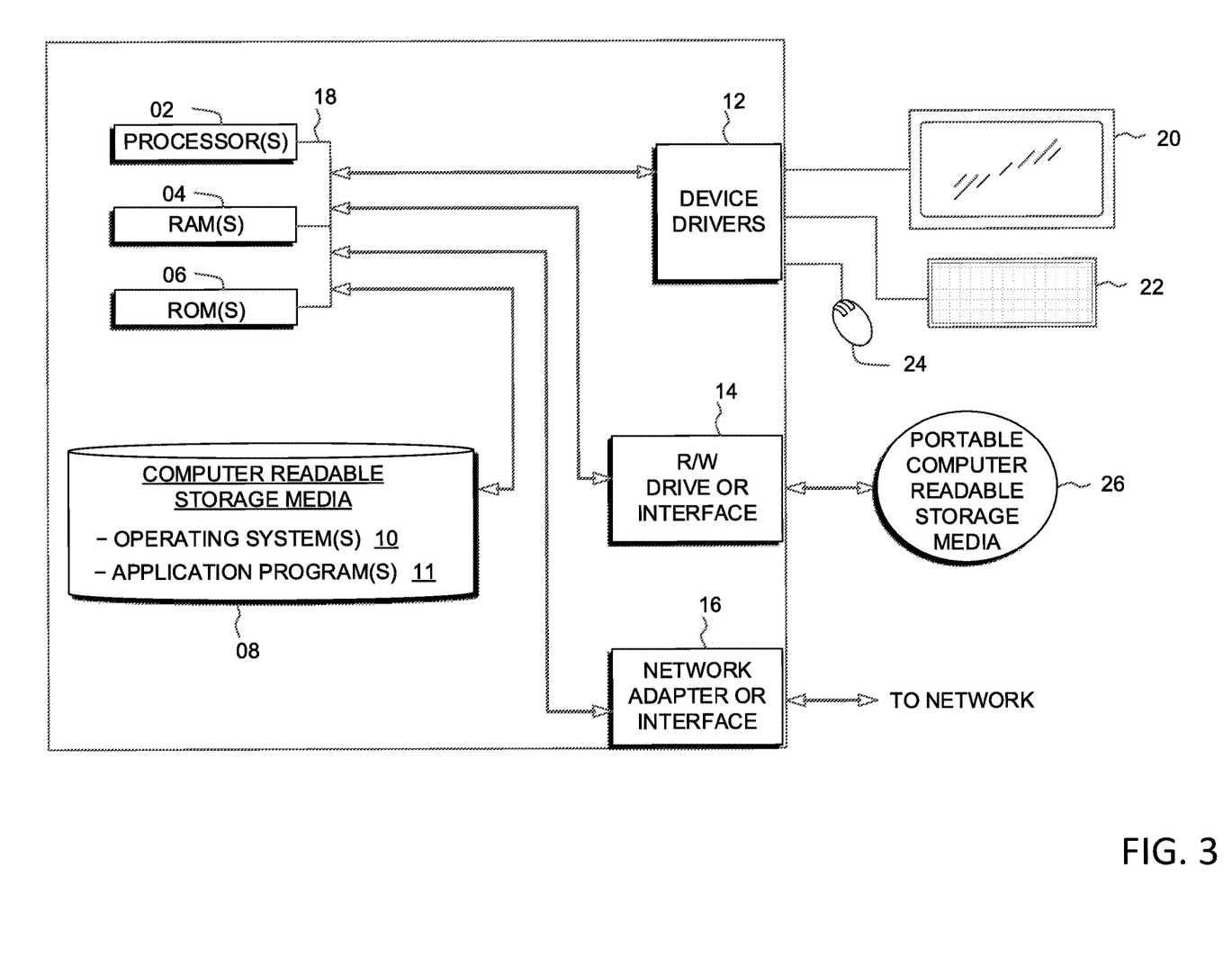
FIG. 3 depicts an exemplary block diagram depicting the hardware components of the digital twin management system 100 of FIG. 1, in accordance with the exemplary embodiments.

FIG. 3 depicts a block diagram of devices used within the digital twin management system 100 of FIG. 1, in accordance with the exemplary embodiments. It should be appreciated that FIG. 3 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
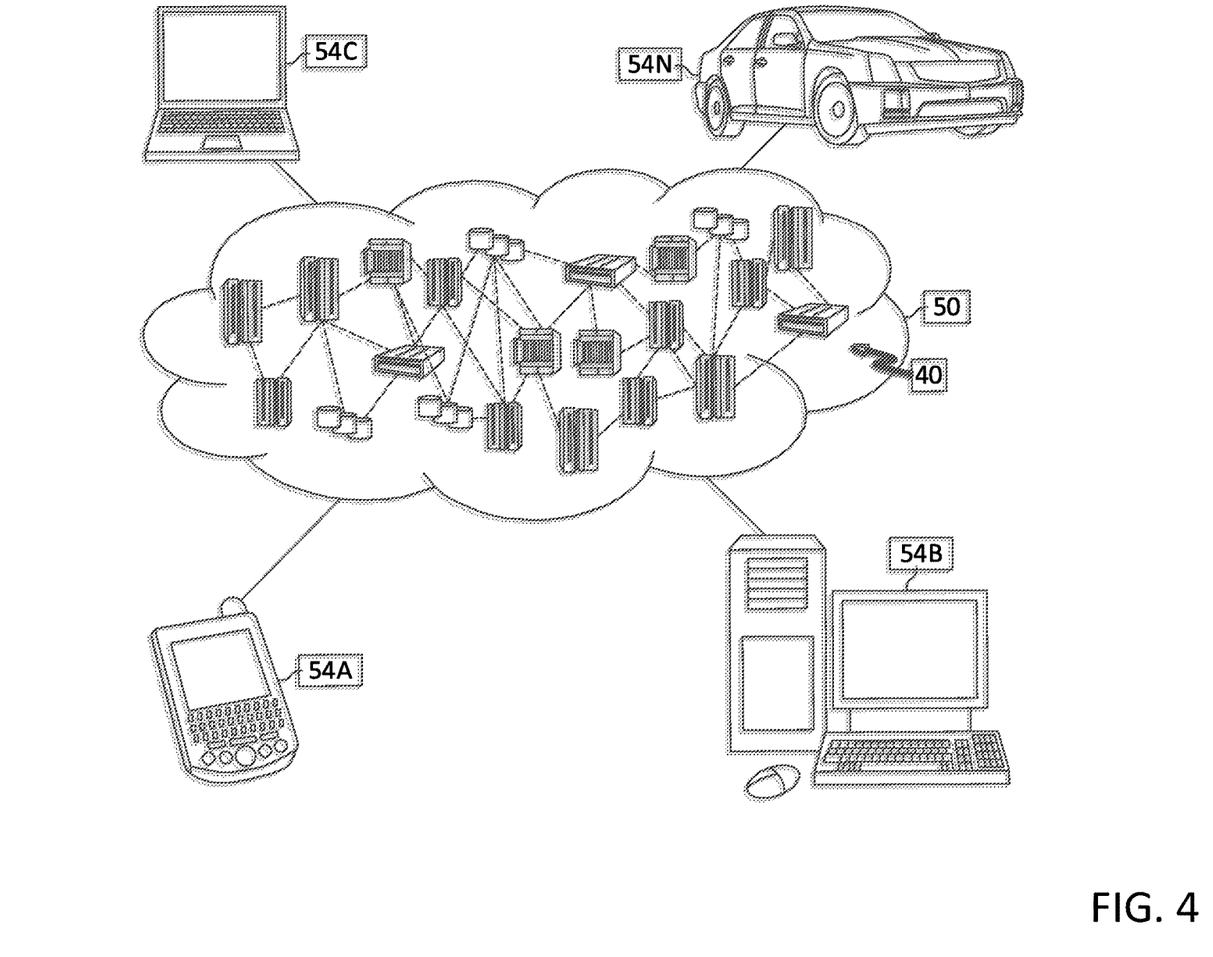
FIG. 4 depicts a cloud computing environment, in accordance with the exemplary embodiments.

Referring now to FIG. 4, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 40 and cloud computing environment 50 can communicate with any type of computerized device over any type of network and/or network addressable connection (e.g., using a web browser).

Figure 5:
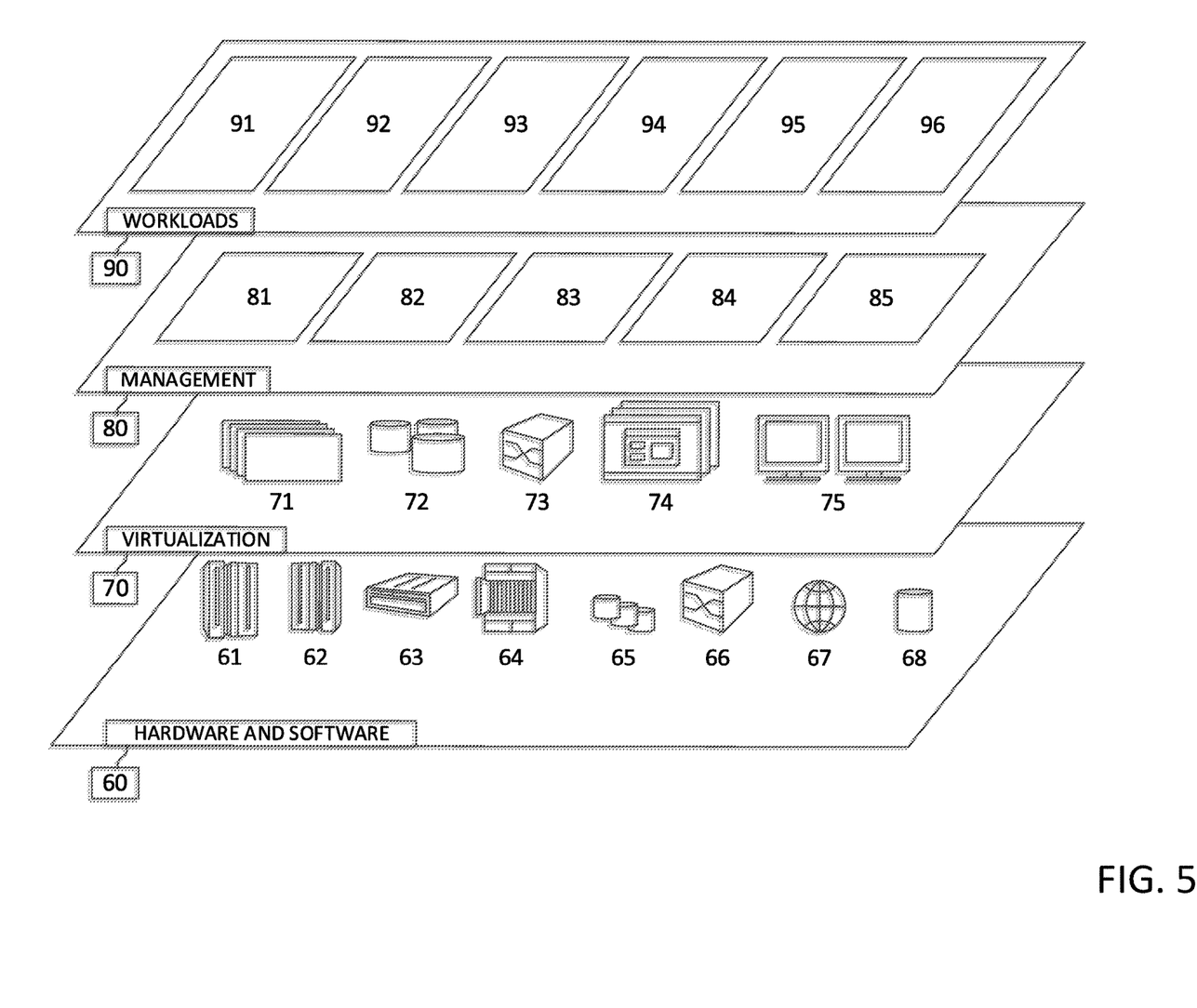
FIG. 5 depicts abstraction model layers, in accordance with the exemplary embodiments.

Referring now to FIG. 5, a set of functional abstraction layers provided by cloud computing environment 50 (FIG. 4) is shown. It should be understood in advance that the components, layers, and functions shown in FIG. 5 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and digital twin processing 96.

The exemplary embodiments may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for managing digital twins, the method comprising:
   gathering data corresponding to one or more bodily tissues corresponding to a patient;
   generating one or more digital twin versions of the one or more bodily tissues that detail the one or more bodily tissues at different ages of the patient;
   identifying compatibilities of the one or more digital twin versions with one or more other body parts of the patient;
   determining that the patient requires a replacement of the one or more bodily tissues;
   identifying from a repository of the one or more digital twin versions a digital twin version based on performing an optimization function, wherein the optimization function optimizes a combination of degree of tissue compensation expected before failure and risk associated with compensation;
   selecting the digital twin version; and
   distributing the digital twin version.

2. The method of claim 1, wherein identifying the digital twin version further comprises:
   extracting one or more health features and one or more compatibility features from the gathered data; and
   computing a health score and a compatibility score based on the one or more extracted features and one or more models.

3. The method of claim 1, wherein distributing the digital twin version further comprises:
   printing the digital twin version.

4. The method of claim 1, further comprising:
   periodically regathering data corresponding to the one or more bodily tissue;
   generating one or more subsequent digital twin versions; and
   detecting an evolution of the one or more bodily tissue by identifying changes between the one or more digital twin versions and the one or more subsequent digital twin versions.

5. The method of claim 1, wherein gathering the data corresponding to the one or more bodily tissue is performed by at least one of a magnetic resonance imaging (MRI) device, a positron emission tomography (PET) device, an x-ray device, a CT scan device, a CAT scan device, an ultrasound device, an echocardiography device, an electroencephalograph (EEG/EcoG) device, a magnetoencephalography (MEG) device, and an electrocardiograph (ECG) device.

6. The method of claim 1, wherein determining that the patient requires the replacement of the one or more bodily tissues is based on at least one of, with respect to the one or more bodily tissue, a certainty of eventual failure, risk of replacement, degree of tissue compensation expected before failure, and risk associated with the tissue compensation.

7. A computer program product for managing digital twins, the computer program product comprising:
one or more non-transitory computer-readable storage media and program instructions stored on the one or more non-transitory computer-readable storage media capable of performing a method, the method comprising:
gathering data corresponding to one or more bodily tissues corresponding to a patient;
generating one or more digital twin versions of the one or more bodily tissues that detail the one or more bodily tissues at different ages of the patient;
identifying compatibilities of the one or more digital twin versions with one or more other body parts of the patient;
determining that the patient requires a replacement of the one or more bodily tissues;
identifying from a repository of the one or more digital twin versions a digital twin version based on performing an optimization function wherein the optimization function optimizes a combination of certainty about eventual failure and risk of replacement of the bodily tissues;
selecting the digital twin version; and
distributing the digital twin version.

8. The computer program product of claim 7, wherein identifying the digital twin version further comprises:
extracting one or more health features and one or more compatibility features from the gathered data; and
computing a health score and a compatibility score based on the one or more extracted features and one or more models.

9. The computer program product of claim 7, wherein distributing the digital twin version further comprises:
printing the digital twin version.

10. The computer program product of claim 7, further comprising:
periodically regathering data corresponding to the one or more bodily tissue;
generating one or more subsequent digital twin versions; and
detecting an evolution of the one or more bodily tissue by identifying changes between the one or more digital twin versions and the one or more subsequent digital twin versions.

11. The computer program product of claim 7, wherein gathering the data corresponding to the one or more bodily tissue is performed by at least one of a magnetic resonance imaging (MRI) device, a positron emission tomography (PET) device, an x-ray device, a CT scan device, a CAT scan device, an ultrasound device, an echocardiography device, an electroencephalograph (EEG/EcoG) device, a magnetoencephalography (MEG) device, and an electrocardiograph (ECG) device.

12. The computer program product of claim 7, wherein determining that the patient requires the replacement of the one or more bodily tissues is based on at least one of, with respect to the one or more bodily tissue, a certainty of eventual failure, risk of replacement, degree of tissue compensation expected before failure, and risk associated with the tissue compensation.

13. A computer system for managing digital twins, the system comprising:
one or more computer processors, one or more computer-readable storage media, and program instructions stored on the one or more of the computer-readable storage media for execution by at least one of the one or more processors capable of performing a method, the method comprising:
gathering data corresponding to one or more bodily tissues corresponding to a patient;
generating one or more digital twin versions of the one or more bodily tissues that detail the one or more bodily tissues at different ages of the patient;
identifying compatibilities of the one or more digital twin versions with one or more other body parts of the patient;
determining that the patient requires a replacement of the one or more bodily tissues;
identifying from a repository of the one or more digital twin versions a digital twin version based on performing an optimization function, wherein the optimization function optimizes a combination of degree of tissue compensation expected before failure and risk associated with compensation;
selecting the digital twin version; and
distributing the digital twin version.

14. The computer system of claim 13, wherein identifying the digital twin version further comprises:
extracting one or more health features and one or more compatibility features from the gathered data; and
computing a health score and a compatibility score based on the one or more extracted features and one or more models.

15. The computer system of claim 13, wherein distributing the digital twin version further comprises:
printing the digital twin version.

16. The computer system of claim 13, further comprising:
periodically regathering data regarding the one or more bodily tissue;
generating one or more subsequent digital twin versions; and
detecting an evolution of the one or more bodily tissue by identifying changes between the one or more digital twin versions and the one or more subsequent digital twin versions.

17. The computer system of claim 13, wherein gathering the data corresponding to the one or more bodily tissue is performed by at least one of a magnetic resonance imaging (MRI) device, a positron emission tomography (PET) device, an x-ray device, a CT scan device, a CAT scan device, an ultrasound device, an echocardiography device, an electroencephalograph (EEG/EcoG) device, a magnetoencephalography (MEG) device, and an electrocardiograph (ECG) device.

18. The computer system of claim 13, wherein determining that the patient requires the replacement of the one or more bodily tissues is based on at least one of, with respect to the one or more bodily tissue, a certainty of eventual failure, risk of replacement, degree of tissue compensation expected before failure, and risk associated with the tissue compensation.

* * * * *